United States Patent [19]

Miwa

[11] Patent Number: 5,841,502

[45] Date of Patent: Nov. 24, 1998

[54] OPHTHALMIC APPARATUS

[75] Inventor: Tetsuyuki Miwa, Aichi, Japan

[73] Assignee: Nidek Co., Ltd., Japan

[21] Appl. No.: 982,255

[22] Filed: Dec. 1, 1997

[30] Foreign Application Priority Data

Nov. 29, 1996 [JP] Japan .................................. 8-334591

[51] Int. Cl.⁶ ..................................................... A61B 3/13
[52] U.S. Cl. ............................................................ 351/209
[58] Field of Search ..................................... 351/205, 208, 351/209, 245, 246; 600/558, 489

[56] References Cited

U.S. PATENT DOCUMENTS

| 5,360,010 | 11/1994 | Applegate et al. ..................... 600/558 |
| 5,387,952 | 2/1995 | Byer ........................................ 351/208 |
| 5,532,769 | 7/1996 | Miwa et al. ............................ 351/205 |

FOREIGN PATENT DOCUMENTS

| 0 310 045 | 4/1989 | European Pat. Off. . |
| 293659 | 4/1996 | United Kingdom . |

*Primary Examiner*—George Manuel
*Attorney, Agent, or Firm*—Finnegan, Henderson, Farabow, Garrett & Dunner, L.L.P.

[57] ABSTRACT

An ophthalmic apparatus including measuring device, comprises a moving device for moving the measuring device relatively to the eye, an alignment detecting device for detecting alignment condition between the measuring device and the eye by projecting an alignment target to the eye, then detecting an image of the target, a movement-controlling device for performing alignment by driving and controlling the moving device based on the detected results, a returning device for causing the measuring device to return to a standard position, a returning-instruction device for instructing the returning device to start movement, a returning-control device for controlling movement of the returning device in response to instruction by the returning-instruction device, a risk sensing device for sensing whether there is risk that the apparatus touches the eye caused by movement of the returning device, and a prohibiting device for prohibiting the returning device from moving to all or predetermined directions at the time when the risk sensing device senses that there is risk that the apparatus touches the eye.

20 Claims, 8 Drawing Sheets

OPHTHALMIC APPARATUS

BACKGROUND OF THE INVENTION

1. Field of the Invention

The present invention relates to an ophthalmic apparatus, and more particularly to the apparatus for adjusting to be a predetermined positional relationship relative to an eye to be examined, then performing inspection or measurement such as measurement of a refractive power of an eye, measurement of an intraocular pressure or the like.

2. Description of Related Art

An ophthalmic apparatus such as a refractive power measuring apparatus which measures a refractive power of en eye to be examined and a noncontact tonometer which measures an intraocular pressure without contacting needs alignment adjustment in order to cause a measuring device to be a predetermined positional relationship relative to the eye. In conventional art, an examiner operates a joystick or the like, by which alignment adjustment was performed, however, recently, such apparatus has been proposed that can perform alignment automatically so that an examiner not skilled in inspecting may perform alignment easily. The apparatus detects alignment condition of the eye fixed to a predetermined position, then driving and controlling the measuring device to move relatively with respect to the eye based on the detected results.

As is described, referring to the apparatus which performs alignment automatically, it is preferable that the measuring device secures a sufficient moving range for moving in order to perform next measurement of the eye, therefore the measuring device, which are made to be moved relatively, is configured so as to return to a standard position in response to a finish signal for measurement. A switch signal generated by using some kinds of switches such as a clear switch used for clearing the measured data and a print switch, or a changing signal for changing right or left eye, are utilized as the finish signal for measurement.

However, by accident, the examiner pushes the clear switch or the print switch during measurement. In the case that a face of an examinee is close to the measuring device, once the measuring device returns to the standard position in response to those signals, in part of the measuring device may touch the face with depending on moving direction.

SUMMARY OF THE INVENTION

The present invention has been made in view of the above circumstances and has an object to overcome the above problems and to provide an ophthalmic apparatus, which may decrease uneasiness of the examinee and protect the examinee in safety with avoiding that the device approaches toward the face unnecessarily.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the present invention, as embodied and broadly described herein, an ophthalmic apparatus including measuring means for measuring or inspecting an eye to be examined, comprises moving means for moving the measuring means relatively to the eye, alignment detecting means for detecting alignment condition between the measuring means and the eye by projecting an alignment target to the eye, then detecting an image of the target which is projected, movement-controlling means for performing alignment by driving and controlling the moving means based on results detected by the alignment detecting means, returning means for causing the measuring means, which is moved by the moving means, to return to a standard position, returning-instruction means for instructing the returning means to start movement, returning-control means for controlling movement of the returning means in response to instruction by the returning-instruction means, risk sensing means for sensing whether there is risk that the apparatus touches the eye caused by movement of the returning means, and prohibiting means for prohibiting the returning means from moving to all or predetermined directions at the time when the risk sensing means senses that there is risk that the apparatus touches the eye.

In another aspect of the present invention, an ophthalmic apparatus including measuring means for measuring or inspecting an eye to be examined, comprises moving means for moving the measuring means relatively to the eye, an alignment target projecting optical system for projecting an alignment target onto the eye, an alignment target detecting optical system for detecting alignment condition between the measuring means and the eye by sensing an image of the target which is projected onto the eye via the alignment target projecting optical system, movement-controlling means for performing alignment by driving and controlling the moving means based on results detected by the alignment target detecting optical system, judging means for judging whether the apparatus is close to the eye based on alignment information given by the alignment target detecting optical system at the time when an instruction signal for return is generated, and prohibiting means for prohibiting the measuring means from returning to a standard position at the time when the judging means judges that the apparatus is close to the eye.

According to the present invention, it is capable of avoiding that the device approaches toward the face unnecessarily, thereby the examinee may be protected in safety.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

A detailed description of one preferred embodiment of an ophthalmic apparatus embodying the present invention will now be given referring to the accompanying drawings.

[Whole schematic configuration]

Figure 1:
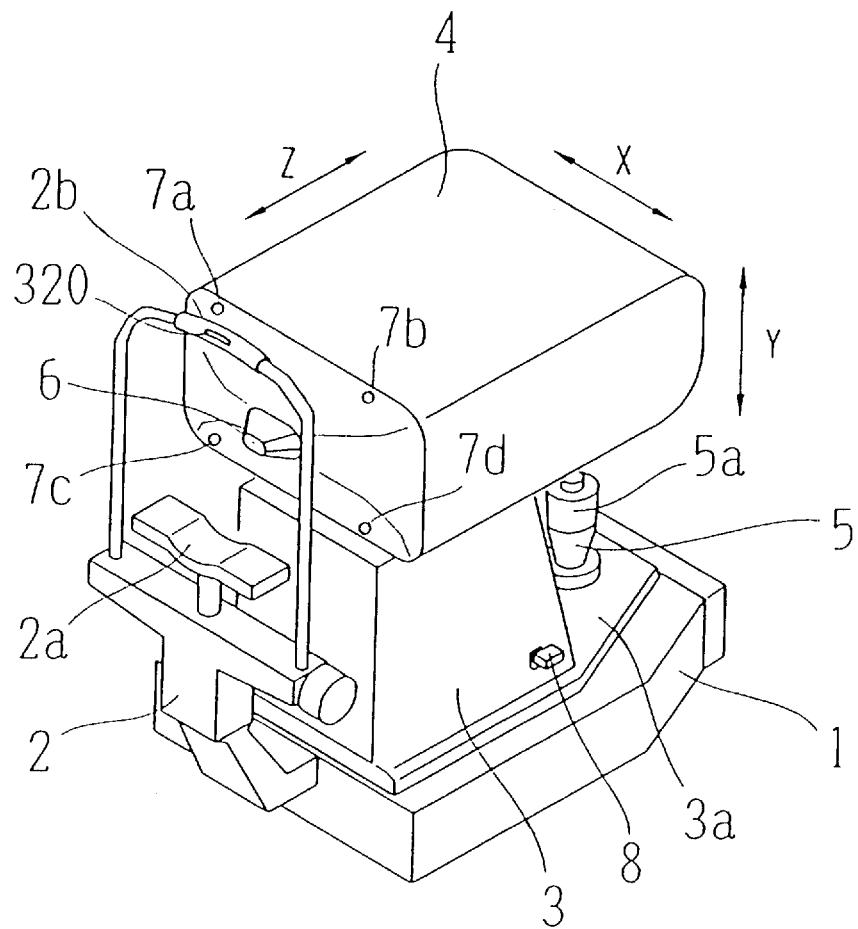
FIG. 1 is an overview of a noncontact tonometer of the preferred embodiment of the present invention.

FIG. 1 is an overview of a noncontact tonometer of the preferred embodiment of the present invention. Reference numeral 1 is a stand to which a face supporter 2 for supporting a face of an examinee is fixed. The face supporter 2 comprises a chin rest 2a for putting a chin of the examinee, and a forehead plate 2b for holding a forehead against there.

At the time of measuring, an eye to be examined is made to be fixed by making the face of the examinee be held against the chin rest 2a and the forehead plate 2b. 320 is a touch sensor provided for the forehead plate 2b.

3 is a body, 4 is a measuring device which is provided with an optical system mentioned below, and 5 is a joystick used for moving the body 3 and the measuring device 4. The body 3 slides to backward-and-forward direction (Z-direction) and lateral direction (X-direction) on horizontal plane of the stand 1 by operating the joystick 5. Also, the measuring device 4 moves to vertical direction (Y-direction) relative to the body 3 by operating a rotation knob 5a. Furthermore, if a mode of automatic alignment is selected, then the measuring device 4 moves to X,Y,Z-directions respectively relative to the body 3 (a mechanism of moving to respective directions is mentioned below).

6 is a nozzle for spouting compressed gas onto the eye is disposed. On the examinee's side of the measuring device 4, four light sources 7a to 7d, which project alignment targets onto around cornea of the eye, are disposed with the center at the nozzle 6. On the side of the body 3, a button 8 is disposed, which is used for restricting a moving range where the nozzle 6 can approach the eye. Also, on the joystick's side of the body 3 (the examiner's side), TV monitor for observation is provided.

[Configuration of respective parts]

Next, configuration of important elements of the present apparatus will be described by dividing the configuration into a joystick mechanism, a mechanism of the measuring device 4 moving toward Y-direction (vertical direction), a mechanism of the measuring device 4 moving toward X,Z-directions (lateral, and backward-and-forward directions), a mechanism for detecting a standard position and a moving limit in X,Z-directions, a mechanism for detecting either left or right eye and a backward position, a mechanism for restricting movement, an optical system, and a controlling system. In addition, a noncontact tonometer is an apparatus which sprays the cornea of the eye with compressed gas and makes the shape of the cornea change so as to be a predetermined shape, then detects gas pressure directly or indirectly, whereby it measures the intraocular pressure of the eye based on the detected gas pressure thereupon, however, detailed description of a measuring mechanism thereof has little relation to the present invention, therefore its description is to be omitted. Detailed description of measuring mechanism is mentioned in Japanese Patent Laid Open No.4-297226 corresponding to U.S. Pat. No. 5,279,300 filed by the present applicant (title of the invention: noncontact type tonometer), to be referred if necessary.

(A) Joystick mechanism

Figure 2:
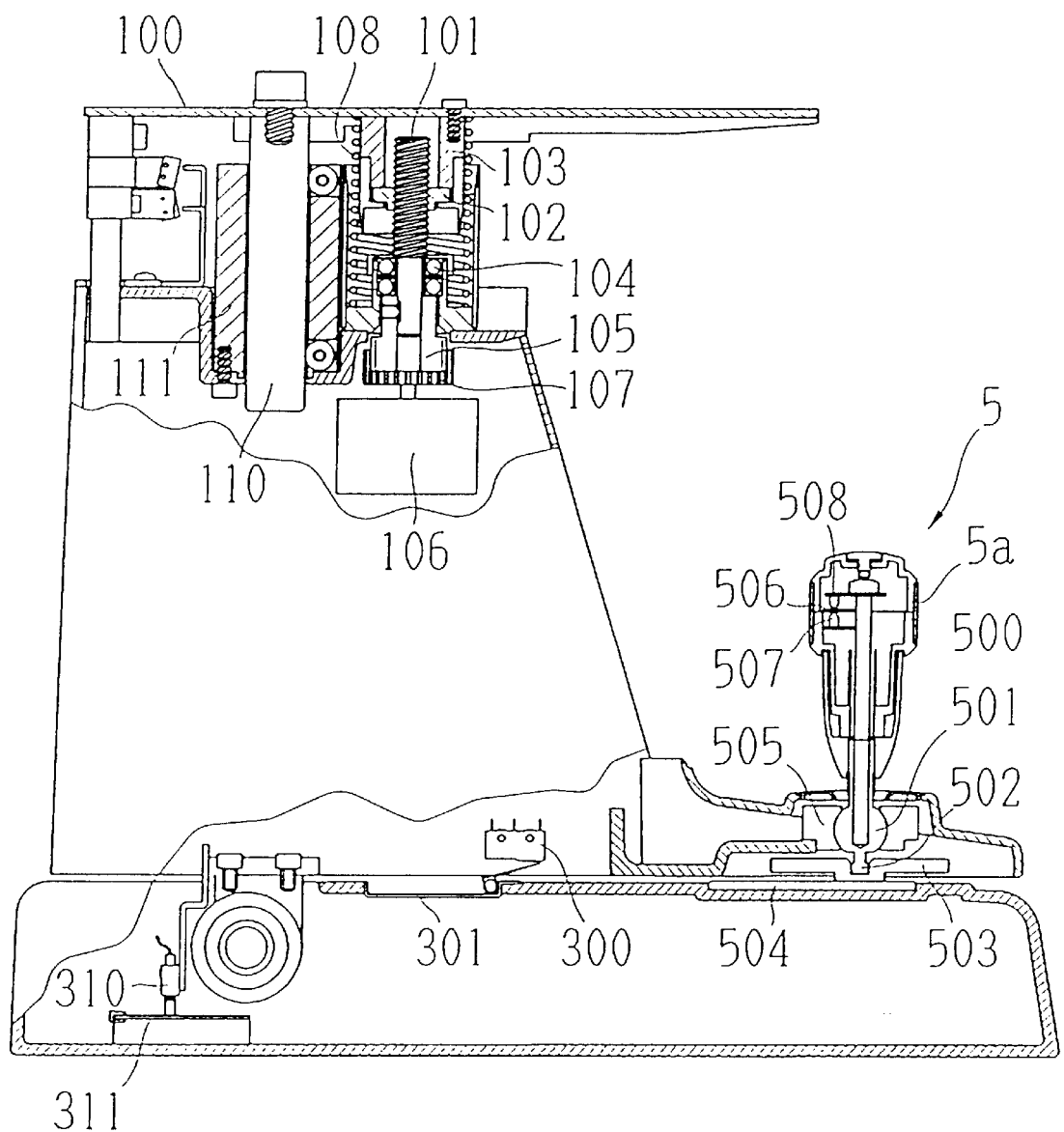
FIG. 2 is a view showing section of important part of a stand and a body including a joystick mechanism shown in FIG. 1.

FIG. 2 shows a section of important part both of the stand 1 and the body 3 including a joystick mechanism. The body 3 can be slightly moved in horizontal direction with respect to the stand 1 caused by configuration of a spherical portion 501 and a lower edge portion 502 which are formed at the lower part of a shaft 500 of the joystick 5, a sliding board 503 at which the lower edge portion 502 swings, a friction board 504 which is adhered on the stand 1 and touches the sliding board 503, and a spherical (ball) bearing 505 inside a housing 3a united with the body 3. Also, the measuring device 4 can be moved in vertical direction with respect to the body 3 by driving and controlling Y-axis motor 106 based on rotating direction and amount of rotation which are detected based on signals from photo-receiving elements (phototransistors) 508 caused by configuration of the rotation knob 5a of the upper part of outer circumference of the joystick 5, a slit plate (disk) 506 which rotates together with the rotation knob 5a, and light sources (LEDs) 507 and the photo-receiving elements (phototransistors) 508 which are provided for the shaft 500 with putting the slit plate (disk) 506 therebetween. Detailed description of a joystick mechanism is mentioned in Japanese Patent Laid Open No. HEI6-7292 corresponding to U.S. Pat. No. 5,406,706 filed by the present applicant, which is to be referred if necessary.

(B) Moving mechanism toward Y-direction (vertical direction)

In FIG. 2, reference numeral 101 is a feed screw, 102 is a feed nut fixed to Y-table 100 by a nut holder 103. On the contrary, the feed screw 101 is held by a case of the body 3 via a bearing 104 so as to rotate at will. A gear 105 is fixed to the lower edge of the feed screw 101, the gear 105 gears into a gear 107 fixed to a rotation shaft of Y-axis motor 106 which is held by the case of the body 3. Also, a pressure spring 108 is mounted between Y-table 100 and the case of the body 3, the pressure spring 108 supports weight of the measuring device 4 mounted on Y-table 100, thereby vertical movement thereof is made to be smooth. 110 is a guide shaft fixed to Y-table 100, and guides movement of Y-table 100 in vertical direction by moving along a guide bearing 111 fixed to the case of the body 3.

By above-mentioned configuration, once Y-axis motor 106 is made to rotate and to drive, then the measuring device 4 mounted on Y-table 100 moves in vertical direction.

(C) Moving mechanism toward X, Z-directions (lateral, backward -and-forward directions)

Figure 3:
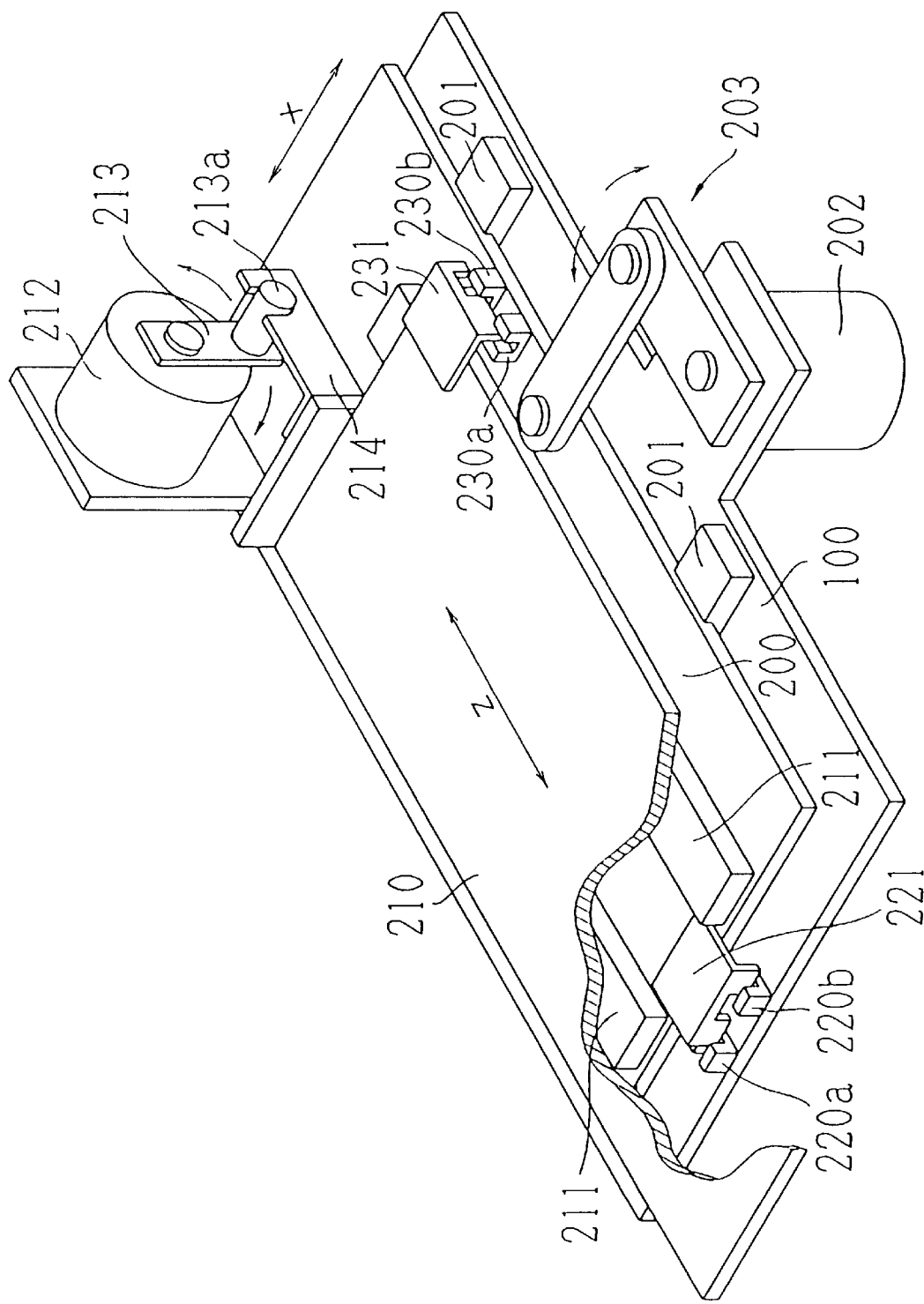
FIG. 3 is a view showing a moving mechanism toward X, Z-directions provided for a measuring device shown in FIG. 1.

FIG. 3 shows a moving mechanism of X, Z-directions provided for the measuring device 4. In FIG. 3, X-table 200 is configured so as to slide in X-direction along two rails 201s which are fixed to above-mentioned Y-table 100. X-axis motor 202 is fixed to Y-table 100, rotation shaft of X-axis motor 202 is connected to X-table 200 via a link 203. Rotation of X-axis motor 202 is transmitted by the link 203 in terms of movement toward X-direction of X-table 200.

Two rails 211s which extend to Z-direction are fixed to X-table 200, Z-table 210 is placed along the rails 211s so as to slide in Z-direction. Movement of Z-table 210 is performed in response to transmission of rotation of Z-axis motor 212 in terms of movement toward Z-direction caused by configuration of Z-axis motor 212 fixed to X-table 200, a decentering cam 213 fixed to a rotation shaft of Z-axis motor 212, and a connecting plate 214, which is formed a gap gearing into a pin 213a of the decentering cam 213, and fixed to a backward edge of Z-table 210. An optical system is arranged on Z-table 210.

Figure 4:
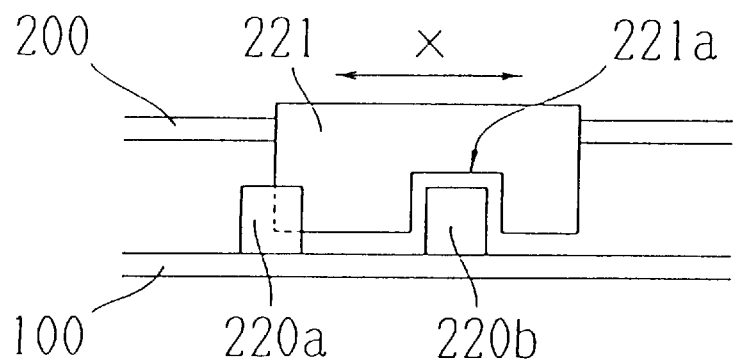
FIG. 4 is a view showing condition of photo sensors and an intercepting plate at the time of detecting a standard position in X-direction shown in FIG. 1.

(D) Mechanism for detecting a standard position and a moving limit in X,Z-directions In FIG. 3, reference numerals 220a and 220b are photo sensors which are arranged on Y-table 100, reference numeral 221 is an intercepting plate fixed to X-table 200. Sensor 220a detects which direction X-table 200 exist with respect to a standard position in X-direction, with depending on a state of light interception caused by the intercepting plate 221, then detects that X-table 200 has been located at the standard position based on a change timing of the state of light interception shown in FIG. 4. In addition, a notch 221a is formed at the intercepting plate 221, and the sensor 220b detects a moving limit of left and right respectively, with depending on a change of the state of light interception caused by the notch 221a corresponding to movement of the intercepting plate 221. Besides, the standard position in X-direction is approximately center of the range where it can move, X-table 200 (that is the measuring device 4) is set so as to move 5 mm respectively with respect to the standard position.

In FIG. 3, reference numerals 230a and 230b are photo sensors which are arranged on X-table 200, reference numeral 231 is an intercepting plate fixed to Z-table 210. Sensors 230a and 230b detect a standard position and a moving limit in Z-direction of Z-table 210, as the same as X-direction, with depending on a state of light interception and a change timing which are caused by the intercepting plate 231 having a notch 231a.

In addition, a moving range in Y-direction is relatively large, therefore, a standard position thereof is not provided in the preferred embodiment, however it may be provided as the same as X,Z-directions.

(E) Mechanism for detecting either left or right eye and a backward position

In FIG. 2, reference numeral 300 is a micro-switch used for detecting a backward edge (examiner's side) held by the body 3, 301 is a guide plate fixed to the stand 1. Once the body 3 comes to the backward edge of a backward-and-forward moving range by operating the joystick 5, then a contact of the micro-switch 300 is pushed up, thereby a current is carried. Also, 310 is a micro-switch used for detecting either left or right eye, which is held by the body 3, 311 is a guide plate fixed to the stand 1. Guide plate 311 extends to lateral direction with respect to the examiner, a right direction (in FIG. 2, an inner part of a view) is higher with a boundary at the center of lateral direction of the stand 1. Micro-switch 310 detects either left or right eye based on ON/OFF state. Detecting signals of these micro-switches 300 and 310 are utilized as instruction signals in order to cause the measuring device 4 to return to the standard position.

(F) Mechanism for restricting movement

Figure 9:
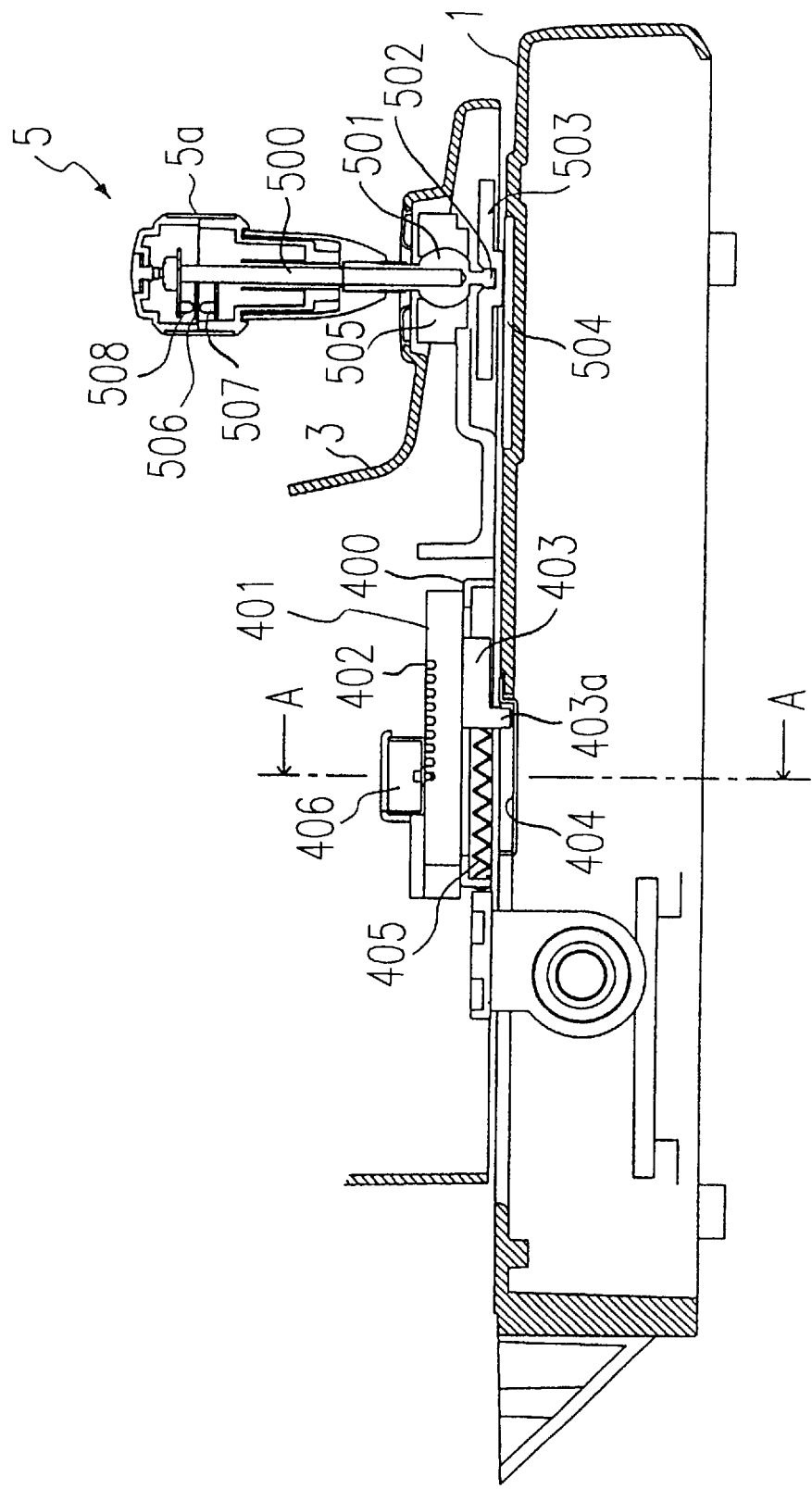
FIG. 9 is a view showing a section of an important part for illustrating mechanism which restricts a moving range in which the body moves.
Figure 10:
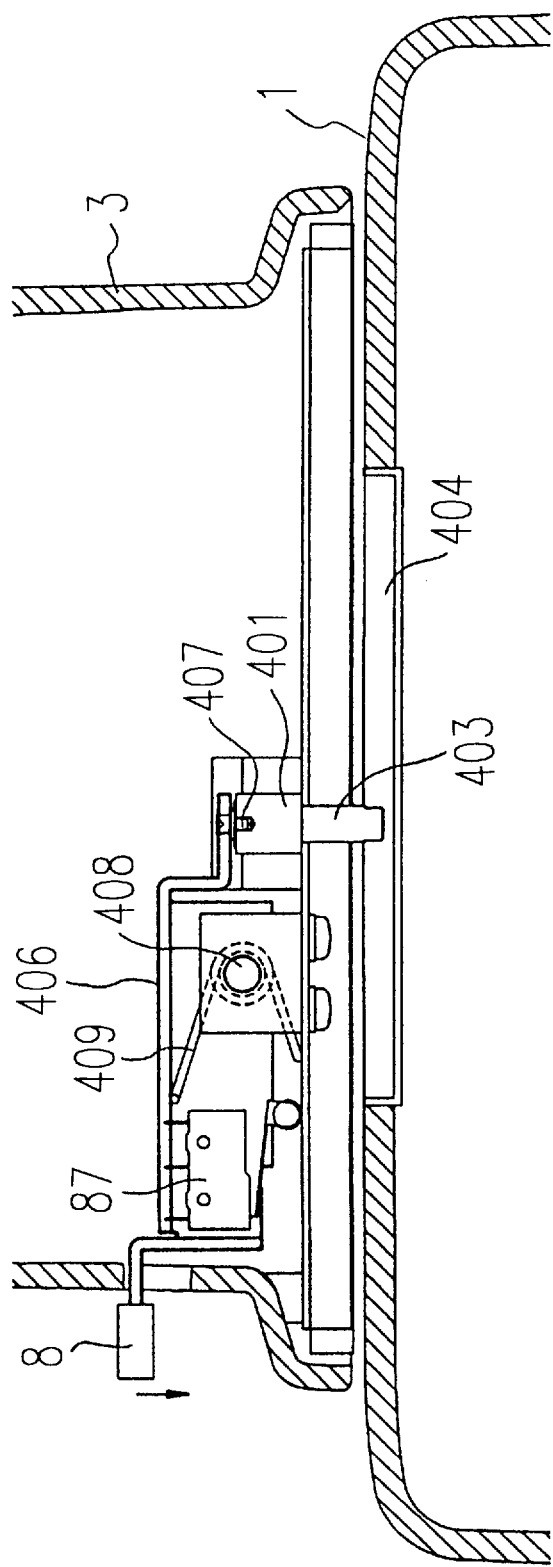
FIG. 10 is a view showing a section denoted by line A—A in FIG. 9.

FIG. 9 shows a section of an important part for illustrating a mechanism which restricts a backward-and-forward moving range in which the body 3 moves, FIG. 10 shows a section denoted by line A—A in FIG. 9. Reference numeral 400 is a base used for holding a mechanism for restricting movement, which is fixed to underside of the body 3, a member 401 for restricting position is held by the base 400 so that the member 401 may move in backward-and-forward direction.

This member 401 for restricting position is provided with nine pin holes 402s at the regular intervals in backward-and-forward direction (something like a gap may be substituted for the pin holes 402s). A stopper 403 is fixed to underside the member 401 for restricting position. Stopper 403 is provided with a protrusion 403a which protrudes to below, the protrusion 403a enters into a hollow 404 provided for the stand 1, whereby the moving range is restricted. That is, restriction of the backward-and-forward moving range is determined by relative positional relationship between the stopper 403 and a wall of the hollow 404.

405 is a spring which energizes the stopper 403 to the examinee's side. 406 is a lever which has the button 8 at one edge, and a pin 407, which is put in the pin hole 402, at another edge. Lever 406 is held by a spindle 408, which is arranged on the base 400, so as to rotate. 409 is a torsional spring which energizes the lever 406 to be repulsive at the time of pushing the button 8 down. Once the button 8 is pushed down, then the pin 407 is lifted, thereby a position of the pin hole 402, in which the pin 407 is put, can be changed.

87 is a micro-switch fixed to underside of the lever 406, the micro-switch 87 carries current once the button 8 is pushed down, then detects that a restricting position is being adjusted. Detecting signal of the micro-switch 87 is also utilized for causing the measuring device 4 to return to the standard position (which is mentioned below).

(G) Optical system

Figure 5:
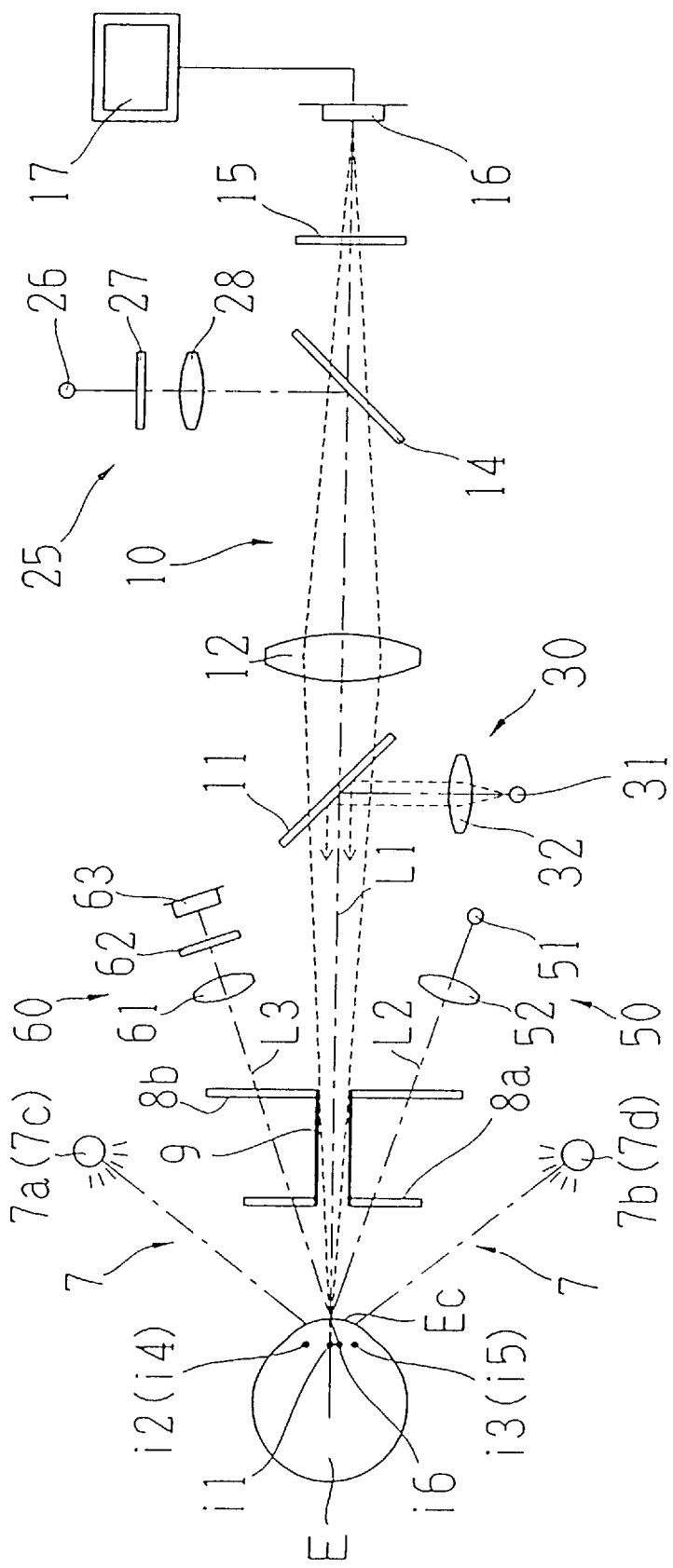
FIG. 5 is a top view showing a schematic construction of an alignment optical system included by the measuring device shown in FIG. 1.

FIG. 5 shows a top view of a schematic construction of an alignment optical system included by the measuring device 4.

On an optical axis L1 of an observation optical system 10, a nozzle hole 9 of the nozzle 6, which spouts gas for changing the shape of the cornea, is disposed with being held by glass plates 8a and 8b, an axis thereof coincides with the optical axis L1.

On the optical axis L1, a beam splitter 11, an objective lens 12, a beam splitter 14, a filter 15 and CCD camera 16 are disposed. Observation optical system 10 serves as a target detecting optical system which detects targets of first and second target projecting optical systems (which is mentioned below) for alignment of vertical and lateral directions. Filter 15 has such characteristics that transmits light bundles (wavelength 950 nm) of targets caused by light sources 31 and 7a to 7d, and does not transmit visible rays and a light bundle of target caused by a light source 51 (wavelength 800 nm), thereby the filter 15 prohibits needless noise lights from entering CCD camera 16. Images of an anterior portion of the eye and targets are displayed on TV monitor 17.

25 is a fixation target optical system. A light bundle from a fixation target plate 27 illuminated by a light source 26 is transmitted to the eye passing through the nozzle hole 9 via a projection lens 28, the beam splitter 14, the objective lens 12 and the beam splitter 11.

30 denotes the first target projecting optical system. Infrared light bundle having wavelength of 950 nm, emitted from the light source 31, is made to be a parallel light bundle by a projection lens 32, then is reflected by the beam splitter 11 and passes through the nozzle hole 9 along the optical axis L1, then travels toward a cornea Ec of the eye. Light bundle mirrored by the cornea Ec forms a target i1 which is a virtual image of the light source 31. The second alignment target projecting optical system 7 includes the four light sources 7a to 7d (see FIG. 1), which emit the infrared light having wavelength of 950 nm. Respective light sources 7a to 7d illuminate periphery of the cornea Ec from four oblique directions, then form respective targets i2, i3, i4 and i5. Also, the light sources 7a to 7d serve as light sources for illuminating the anterior portion of the eye. Light bundles of the targets i1 to i5 are transmitted to CCD camera 16 via the observation optical system 10, and form images on photographing elements of CCD camera 16.

50 is a distance target projecting optical system, and 60 is a distance target detecting optical system. An optical axis L2 of the distance target projecting optical system 50 and an optical axis L3 of the distance target detecting optical system 60 are disposed so as to be symmetric and to incline with respect to the optical axis L1, therefore the optical axes L2 and L3 intersect at a position being apart from the nozzle hole 9 at a predetermined working distance. Light having wavelength of 800 nm, emitted from a light source 51, is made to be a parallel light bundle by a projection lens 52, and is transmitted to the cornea Ec along the optical axis L2, then forms a target i6. Light bundle of the target i6 enters an one-dimensional photodetector 63 via a photo-receiving lens 61 and a filter 62. Filter 62 has such characteristics that transmits a light bundle of the light source 51 (wavelength 800 nm) and does not transmit light bundles of the light sources 7a to 7d and 31 (wavelength 950 nm), thereby the filter 62 prohibits noise lights from entering the one-dimensional photodetector 63.

(H) Controlling system

Figure 6:
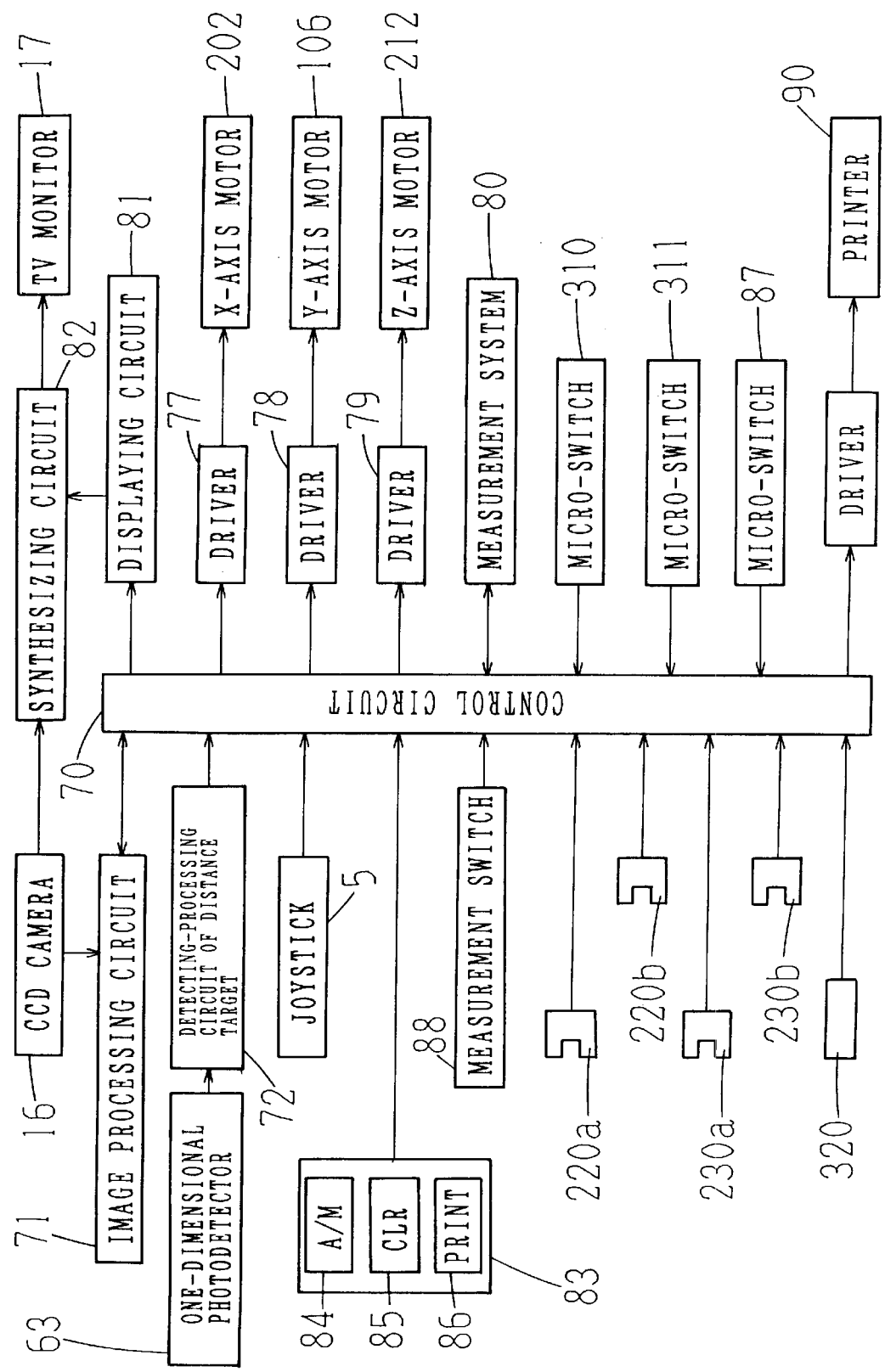
FIG. 6 is a view showing construction of an important part of a control system of the preferred embodiment of the present invention.

FIG. 6 shows construction of an important part of a control system of the apparatus of the preferred embodiment. 70 is a control circuit, 71 is an image processing circuit, 72 is a detecting-processing circuit of the distance target, 80 is a measurement system, 81 is a displaying circuit for generating a character information and a reticle, and 82 is a synthesizing circuit. 83 is a switch group, which includes an alignment mode-changing switch 84 used for selecting either an automatic alignment performed by the apparatus based on detection of target or a manual alignment performed by the examiner by using only the joystick 5, a clear switch 85 for clearing measured data, and a print switch 86 for printing out measured results from a printer 90.

Image processing circuit 71 gives image processing to the images photographed by CCD camera 16, and inputs processing results thereof into the control circuit 70. Control circuit 70 obtains positional information of the target images and that of the pupil based on inputted signals thereof. Also, the control circuit 70 obtains information of deviation in backward-and-forward direction with respect to the eye E based on signals from the one-dimensional photodetector 63, inputted via the detecting-processing circuit 72. Information of deviation which is obtained by the control circuit 70 is transmitted to the displaying circuit 81, and the displaying circuit 81 generates a signal of a figure and a signal of a position on TV monitor 17 of a distance mark based on the information. A signal outputted from the displaying circuit 81 is synthesized with an image signal from CCD camera 16 by the synthesizing circuit 82, then is displayed on TV monitor 17.

Figure 7:
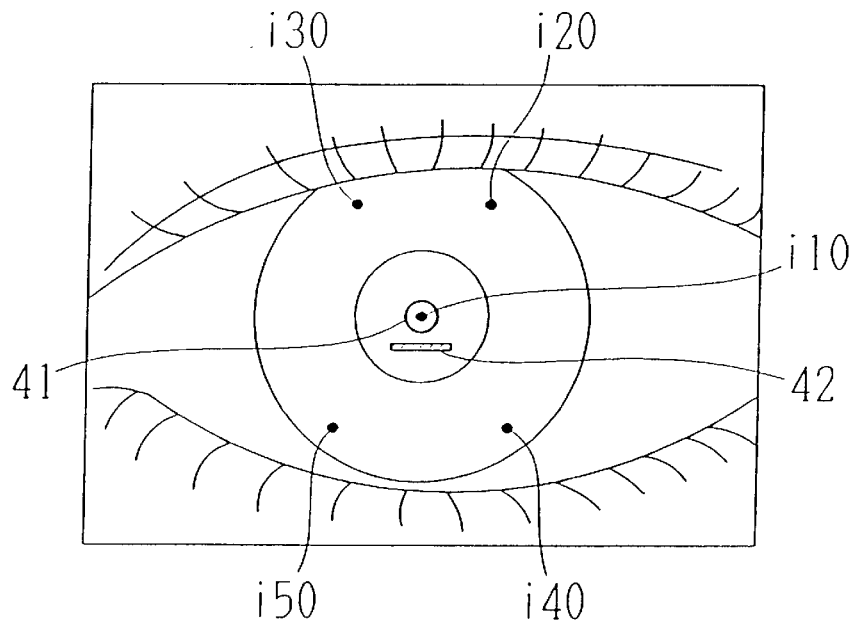
FIG. 7 is a view showing an example of a picture displayed on TV monitor 17 at the time when X,Y-directions, shown in FIG. 1, is aligned so as to be appropriate condition.

FIG. 7 shows an example of a picture displayed on TV monitor 17 when X,Y-directions are aligned to be appropriate condition. In the case that X,Y-directions are aligned to be the appropriate condition, four target images i20, i30, i40 and i50 which are formed around the cornea by the second alignment target projecting optical system and a target image i10 which is formed approximately center of the cornea by the first alignment target projecting optical system are displayed. 41 denotes a reticle image which is formed by a reticle optical system which is not shown (the reticle image 41 can be formed under electrical control). 42 denotes the distance mark, which moves over the reticle image 41 in real-time in corresponding to a distance between the cornea of the eye and the nozzle 6, if the cornea is at an appropriate working distance, then the distance mark 42 is superposed on the reticle image 41.

The operation having such architecture will be described hereinafter. Firstly, alignment operation of the apparatus under an automatic alignment mode will be described.

The examiner fixes the face of the examinee to the face supporter 2, and then performs positional adjustment of a restricting position in forward direction depending on the position of the eye by using the mechanism for restricting movement. The examiner pushed the button 8 down, thereby the pin 407 is removed from the pin hole 402 of the member 401 for restricting position. Once the button 8 is pushed down, then the micro-switch 87 detects it, and generates an instruction signal for return, thereby the measuring device 4 is made to be returned to respective standard positions in X,Z-directions (returning to the standard position is mentioned below). In addition, the micro-switch 87 generates a signal, which indicates that positional adjustment is in progress while the button 8 is being pushed down, and causes working of the automatic alignment to stop. Such message may be also displayed on TV monitor 17 that positional adjustment is in progress (it may be informed of the examiner by sound).

Continuously, the body 3 is made to move to backward-and-forward and lateral directions by operating the joystick 5, then the nozzle 6 is positioned, in advance, at which the position is closer to the examinee than the appropriate position of measurement to some extent. Stopper 403 is pulled toward the examinee's side by the spring 405, therefore it moves to the position where the protrusion 403a touches the wall of the hollow 404 of the examinee's side. The examiner releases the button 8, and causes the mechanism for restricting movement to be locked by putting the pin 407 into the pin hole 402 where is corresponding to approximately adjusted position. Signal from the micro-switch 87, indicating that the positional adjustment is in progress, is cut in response to putting into the pin hole 402, thereby it is come back to the condition that the automatic alignment can go into run. In addition, detailed description of positional adjustment is mentioned in Japanese Patent Laid Open No.HEI8-266475 filed by the present applicant, which is to be referred.

After the positional adjustment has been completed, the examiner operates the joystick 5, or the like, with observing TV monitor 17, and then aligns the measuring device 4 with respect to the eye roughly. Rough alignment is performed by adjusting X,Y-directions so that at least one of target images, formed by the first and second alignment target projecting optical systems, may appear on TV monitor 17, and is performed by moving the body 3 to the direction of the eye so that the target image, which appears on TV monitor 17 (the image of the anterior portion of the eye), may be brought into focus.

Once the target image is detected, the joystick 5 is made to be stopped being operated. Control circuit 70 judges alignment condition in X,Y-directions based on the number of target images and positional relationships of them which are detected and processed by the image processing circuit 71, then causes the measuring device 4 to move by driving the X-axis motor 202 and Y-axis motor 106, based on the judged results, so that the target image i10 may enter a predetermined permissible range. Also, once the light bundle of the target i6 comes to be transmitted to the one-dimensional photodetector 63, then the control circuit 70 obtains information of deviation in Z-direction based on signals from the one-dimensional photodetector 63, then causes the measuring device 4 to move by driving the Z-axis motor 212 based on the information of deviation (details concerning these movement is mentioned in Japanese Patent Application No. HEI8-188564 corresponding to U.S. patent application Ser. No. 08/883,102 filed by the present applicant to be referred). When respective alignment in X,Y,Z-directions come to be appropriate condition, then the control circuit 70 causes the measuring device 4 to stop moving, and generates a starting signal of measurement automatically allowing the measurement system 80 to execute measurement. Measured results are displayed on TV monitor 17.

Figure 8:
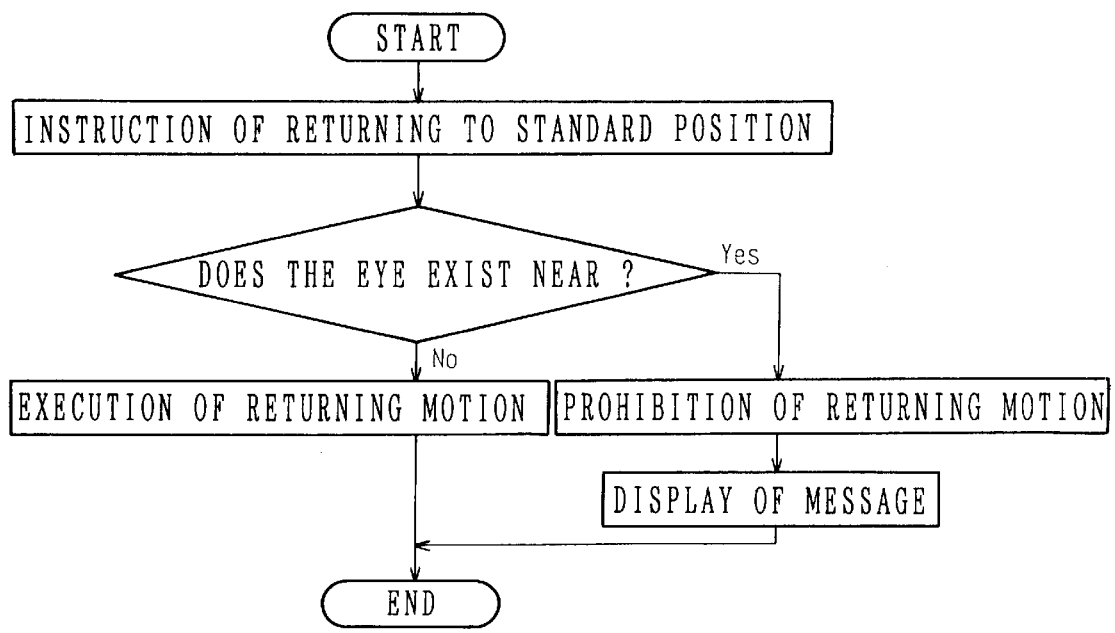
FIG. 8 is a flowchart for illustrating operation to cause the measuring device, shown in FIG. 1, to return to a standard position.

Next, operation for causing the measuring device 4 to return to the standard position will be described (see FIG. 8). Instruction signal for return, which causes the measuring device 4 to return to respective standard positions in X,Z-directions, is generated at the time of detecting that the positional adjustment is started (the button 8 is pushed down) by the micro-switch 87, at the time when the clear switch 85 or the print switch 86 is pushed down, at the time when the backward edge of the backward-and-forward moving range of the body 3 is detected by the micro-switch 300, and at the time when the change of left and right eyes is detected by the micro-switch 310. Once the instruction signal for return is generated, the control circuit 70 judges whether the eye is close to the nozzle 6 (the measuring device 4) based on alignment information of target images which are formed by target projecting optical systems 30, 7 and 50. If there is still one target image which is detected and processed by the image processing circuit 71 or the detecting-processing circuit 72, then the control circuit 70 judges that the eye is close to the nozzle 6. In the case of the apparatus of the preferred embodiment, target images are formed around the cornea of the eye by the second alignment target projecting optical system 7, and are detected, therefore the eye can be detected within a wide range. In addition, whether the eye is close to the nozzle 6 can be judged by detecting and processing the image of the anterior portion of the eye based on the image captured by CCD camera 16.

If the control circuit 70 judges that the eye is not close to the nozzle 6, then it obtains the directions where the measuring device 4 is positioned with respect to the standard positions in X,Z-directions based on signals from the sensors 220a, 220b, 230a and 230b, respectively, after that the control circuit 70 causes the X-axis motor 202 and Z-axis motor 212 to go into run, whereby the measuring device 4 is made to be moved to respective standard positions with respect to the body 3. If the control circuit 70 judges that the eye is close to the nozzle 6, then it ignores the generated instruction signal for return and prohibits the measuring device 4 from returning to the standard position. At the same time, a message, which indicates prohibition of returning movement, is displayed on TV monitor 17 in order to inform of the examiner (it may be also informed of the examiner by sound). Thereby even when the clear switch 85 or the print switch 86 is pushed down unexpectedly, if the nozzle 6 is close to the eye, then the measuring device 4 is prohibited from returning, therefore, it can avoid touching the face of the examinee. Also, the examiner can understand that returning movement is prohibited, therefore, the examiner can take necessary measures such as avoiding risk of touching in advance by separating the measuring device 4 from the examinee, or the like, easily.

After the message which indicates prohibition of returning movement is displayed on TV monitor 17, in the case that the measuring device 4 is made to return to the standard position, it is described as following. Firstly, the measuring device 4 is made to be separated from the eye by moving the body 3 to backward direction (the examiner's side) by operating the joystick 5. Once the body 3 is made to move to the backward edge, then the micro-switch 300 detects it. Once the body 3 moves to the backward edge, then the distance between the eye and the nozzle 6 becomes enough, and since it is set so that the target image may not be detected by the image processing circuit 71, the control circuit 70 executes returning movement of the measuring device 4 to the standard position in response to the instruction signal for return generated by the micro-switch 300. In addition, even though the body 3 is not made to be moved to the backward edge, if the target image becomes not to be detected (if such a sufficient distance that is not touching the face of the examiner is secured), then returning movement of the measuring device 4 to the standard position is executed by the clear switch 85 or the like.

Instruction signal for return is also generated at the time of changing left and right eyes, thereby returning movement of the measuring device 4 to the standard position is executed. The change of left and right eyes with a noncontact tonometer, of which a working distance is short, is performed by way that the body 3 is made to move to backward direction by operating the joystick 5, therefore a distance is secured so as not to touch the face (in particular a nose) of the examinee, then the body 3 is made to move to lateral direction. At the time of changing left and right eyes, the target image becomes not to be detected, however, referring to the apparatus of the preferred embodiment, a moving range of the measuring device 4 toward the eye in Z-direction is set to be lessen, thereby, even if returning movement is performed based on a changing signal of left and right eyes, it is configured that the nozzle 6 may not touch the face of the examiner at the time of moving to Z-direction.

In the case that the moving range toward Z-direction is enlarged, only the returning movement toward direction close to the examiner may be prohibited. In this case, whether the examinee is under measurement or not, is detected by the touch sensor 320 provided for the forehead plate 2b. Under the condition that the examinee makes his own forehead be held against the forehead plate 2b, only returning movement toward direction being closer to the examiner in Z-direction is prohibited with defining as that the examinee is under measurement.

Furthermore, related to returning movement toward lateral direction, it is proved out that the nozzle 6 is at either left or right side of the face of the examinee by detecting either left or right eye, therefore, only returning movement toward direction being closer to the nose side of the examinee may be prohibited.

In addition, when it is judged by the touch sensor 320 that the examinee is under measurement, then returning movement toward respective directions may be prohibited in response to above-mentioned instruction signal for return.

As described above, in the case that the measuring device 4 returns to respective standard positions in respective directions, if the eye is close to the measuring device 4 (the nozzle 6) or if the examinee is under measurement, then movement toward direction being closer to the examinee is not performed, therefore it is allowed that the examinee does not feel uneasiness.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic apparatus including measuring means for measuring or inspecting an eye to be examined, comprising:

moving means for moving said measuring means relatively to the eye;

alignment detecting means for detecting alignment condition between said measuring means and the eye by projecting an alignment target to the eye, then detecting an image of the target which is projected;

movement-controlling means for performing alignment by driving and controlling said moving means based on results detected by said alignment detecting means;

returning means for causing said measuring means, which is moved by said moving means, to return to a standard position;

returning-instruction means for instructing said returning means to start movement;

returning-control means for controlling movement of said returning means in response to instruction by said returning-instruction means;

risk sensing means for sensing whether there is risk that the apparatus touches the eye caused by movement of said returning means; and prohibiting means for prohibiting said returning means from moving to all or predetermined directions at the time when said risk sensing means senses that there is risk that the apparatus touches the eye.

2. The ophthalmic apparatus according to claim 1, wherein said risk sensing means includes judging means for judging whether there is risk of touching the eye, based on detected condition of the image of the target which is projected onto the eye by said alignment detecting means.

3. The ophthalmic apparatus according to claim 1, further comprising:

face-supporting means for supporting a face of an examinee in order to fix the eye; and face-touch sensing means for sensing that the face touches said face-supporting means;

whereby risk of touching the eye is judged by said risk sensing means based on results sensed by said face-touch sensing means.

4. The ophthalmic apparatus according to claim 1, wherein said moving means includes backward-and-forward moving means for moving to at least backward-and-forward direction relatively to the eye; wherein said returning means includes backward-and-forward direction returning means for causing said measuring means to return to the standard position of said backward-and-forward moving means; and wherein said prohibiting means prohibits at least said measuring means from returning to direction where is coming to be close to the eye caused by said backward-and-forward direction returning means.

5. The ophthalmic apparatus according to claim 1, further comprising:

informing means for informing an examiner of that said returning means is prohibited from moving by said prohibiting means.

6. The ophthalmic apparatus according to claim 1, further comprising:

at least either a clear switch for clearing measured data obtained by executing measurement of said measuring means, or a print switch for printing out measured data;

whereby an instruction signal for return is generated by said returning-instruction means in response to a signal inputted by said switches.

7. The ophthalmic apparatus according to claim 1, further comprising:

left-and-right eye change detecting means for detecting change between left and right eyes based on movement of said moving means;

whereby the instruction signal for return is generated by said returning-instruction means in response to a changing signal inputted by said left-and-right eye change detecting means.

8. The ophthalmic apparatus according to claim 1, further comprising:

backward edge detecting means for detecting that said moving means has moved said measuring means to the most backward relative to the eye;

whereby the instruction signal for return is generated by said returning-instruction means in response to a detecting signal inputted by said backward edge detecting means.

9. The ophthalmic apparatus according to claim 1, further comprising:

restricting means for restricting a moving-range of the eye's direction in which said moving means moves;

changing means for change the moving-range which is restricted by said restricting means; and sensing means for sensing operation caused by said changing means;

whereby an instruction signal for return is generated by said returning-instruction means in response to a sensing signal inputted by said sensing means.

10. The ophthalmic apparatus according to claim 9, wherein said movement-controlling means drives and controls said moving means not to perform the alignment while inputting the sensing signal from said sensing means.

11. The ophthalmic apparatus according to claim 9, further comprising:

warning means for giving warning to an examiner while inputting the sensing signal from said sensing means.

12. An ophthalmic apparatus including measuring means for measuring or inspecting an eye to be examined, comprising:

moving means for moving said measuring means relatively to the eye;

an alignment target projecting optical system for projecting an alignment target onto the eye;

an alignment target detecting optical system for detecting alignment condition between said measuring means and the eye by sensing an image of the target which is projected onto the eye via said alignment target projecting optical system;

movement-controlling means for performing alignment by driving and controlling said moving means based on results detected by said alignment target detecting optical system;

judging means for judging whether the apparatus is close to the eye based on alignment information given by said alignment target detecting optical system at the time when an instruction signal for return is generated; and prohibiting means for prohibiting said measuring means from returning to a standard position at the time when said judging means judges that the apparatus is close to the eye.

13. The ophthalmic apparatus according to claim 12, further comprising:

informing means for informing an examiner of that said measuring means is prohibited from returning by said prohibiting means.

14. The ophthalmic apparatus according to claim 12, further comprising:

measuring condition sensing means for sensing that an examinee is under the condition of measurement;

whereby said measuring means is prohibited from returning by said prohibiting means at the time when it is judged that the examinee is under the condition of measurement based on a signal inputted by said measuring condition sensing means.

15. The ophthalmic apparatus according to claim 12, wherein said moving means comprises a driving mechanism for moving to direction where is coming to be closer and to be further relative to the eye, and a driving mechanism for moving to lateral direction relative to the eye.

16. The ophthalmic apparatus according to claim 15, wherein said driving mechanism for moving to said direction where is coming to be closer and to be further relative to the eye, and said driving mechanism for moving to lateral direction relative to the eye respectively comprising:

position detecting means for detecting that which direction said measuring means exist with respect to a standard position and said measuring means is located at the standard position; and moving-limit detecting means for detecting moving-limit of said measuring means which is moved by said moving means.

17. The ophthalmic apparatus according to claim 15, the apparatus being a noncontact tonometer including a nozzle which spouts compressed gas onto the eye.

18. The ophthalmic apparatus according to claim 12, further comprising:

an observation optical system for observing an image of an anterior part of the eye and an image of the alignment target which is detected by said alignment target detecting optical system, whereby said image of the anterior part of the and the image of the alignment target which are observed by said observation optical system are displayed on TV monitor.

19. The ophthalmic apparatus according to claim 18, wherein said alignment target detecting optical system is shared with said observation optical system.

20. The ophthalmic apparatus according to claim 18, wherein a message which informs of prohibiting from returning is displayed on said TV monitor at the time when said measuring means is prohibited from returning by said prohibiting means.

\* \* \* \* \*

UNITED STATES PATENT AND TRADEMARK OFFICE
CERTIFICATE OF CORRECTION

PATENT NO.: 5,841,502

DATED: November 24, 1998

INVENTOR(S): MIWA, Tetsuyuki

It is certified that an error appears in the above-identified patent and that said Letters Patent is hereby corrected as shown below:

On the title page, in item [56] References Cited, insert the following:

5,279,300   1/1994   Miwa et al.   128/648;
    5,406,076   4/1995   Mimura et al.   250/229;
    U.S. Pat. Appl. 08/883,102 (filing date 06/26/96);

under "References Cited, Foreign Patent Documents" please insert:
    7-231875   9/1995   Japan;
    8-10222   1/1996   Japan;
    8-266475   10/1996   Japan.

Signed and Sealed this

Thirteenth Day of April, 1999

Q. TODD DICKINSON

*Attest:*

*Attesting Officer*      *Acting Commissioner of Patents and Trademarks*